United States Patent [19]

Murrer et al.

[11] Patent Number: 5,093,134
[45] Date of Patent: Mar. 3, 1992

[54] METHOD OF TREATING HIV INFECTION USING POLYOXOMETALLATES

[75] Inventors: Barry A. Murrer; Brian R. C. Theobald; Paul D. Savage, all of Reading, United Kingdom

[73] Assignee: Johnson Matthey Public Limited Company, London, England

[21] Appl. No.: 493,342

[22] Filed: Mar. 14, 1990

[30] Foreign Application Priority Data

Mar. 17, 1989 [GB] United Kingdom ............... 8906189

[51] Int. Cl.$^5$ .................... A61K 33/24; A61K 33/06
[52] U.S. Cl. .................... 424/617; 424/649; 424/650; 424/630; 424/684; 424/646; 424/657; 424/682; 424/601; 514/885
[58] Field of Search ............ 424/617, 604, 630, 641, 424/649, 650, 646, 657, 682, 601; 514/885, 492, 493, 494, 499, 501

[56] References Cited

FOREIGN PATENT DOCUMENTS 6438022 2/1989 Japan.
1385489 2/1975 United Kingdom.

OTHER PUBLICATIONS

Cotton, R. A. and Wilkinson, G., Advanced Inorganic Chemistry, 4th Edition, John Wiley & Sons, 1980, pp. 856-859.
Dagani, R., Efforts Intensify to Develop Drugs, Vaccines That Combat Aids; C & EN Washington, Dec. 8, 1986, pp. 7-14.
Baum, R. M.—Aids Researchers Make Inroads in Understanding A Complex Virus, C & EN, Dec. 1, 1986, pp. 7-12.
Peacock, R. D. and Weakley, T. J. R., Heteropoytungstate Complexes of the Lanthanide Elements, PT. 1., J. Chem. Soc. (A), 1971, pp. 1836-1839.
Sir Geoffrey Wilkinson, Comprehensive Coordination Chemistry, vol. 3, Pergamon Press, "Isopolyanions and Heteropolyanions", Pope, M. T., Chapter 38, pp. 1023-1058.
Kirschner, S., Inorganic Syntheses, vol. 23, John Wiley & Sons, Chapter 38, pp. 186-191.

Primary Examiner—Thurman K. Page
Assistant Examiner—G. S. Kishori
Attorney, Agent, or Firm—Cushman, Darby & Cushman

[57] ABSTRACT

Compounds of the formula, $$A_x[D'(MW_{11}O_{39})_2] \cdot yH_2O$$

in which A is a cation, x is an integer, M is B, Si or P, D is metal and D' is a lanthanide in oxidation state 3 or 4, L is a neutral or anionic ligand, and y is an interger, have anti-viral activity in a standard screen, and may be used to produce compositions and also coated articles and devices for treatment or prophylactic treatment of patients at risk.

2 Claims, No Drawings

METHOD OF TREATING HIV INFECTION USING POLYOXOMETALLATES

This invention concerns improvements in chemical compounds, more especially it concerns pharmaceutical compositions. In particular it concerns compositions and compounds having activity in in vitro tests on Human Immunodeficiency Virus-infected cells.

The disease known as Acquired Immune Deficiency Syndrome (AIDS) caused by infection by HIV has attracted immense research effort because of the effects of the disease on infected individuals and the dangers of the disease spreading to a wider section of the population. In general, although various chemo-therapeutic treatments have been advocated, and some compounds have emerged as a potential basis for treatment, there is still a need for alternatives. In particular, most treatments such as the compound known as AZT have a high toxicity to cells, and it would be desirable to find compounds which are less toxic.

We have found a group of compounds which show interesting properties in in vitro screens of human cells challenged with HIV-1 and/or HIV-2, and are therefore indicated as having potential for the treatment of AIDS and AIDS Related Complex. Accordingly, the present invention provides the use of compounds defined below, in pharmaceutical compositions for treating HIV-infected patients. The invention further provides pharmaceutical compositions comprising a said compound in combination or association with a pharmaceutically acceptable diluent or excipient, for the treatment of HIV-infected patients. The invention may also be defined as the use of a said compound for the manufacture of a medicament for the treatment of HIV-infected patients. The invention further provides a process for the production of a pharmaceutical composition for the treatment of a HIV-infected patient, comprising the combination of a compound as defined below with a pharmaceutically acceptable diluent or excipient, and formulating said composition into a form suitable for adminstration to said patient. The invention also provides a method of treatment of an HIV-infected patient, comprising administering to said patient an effective dose of a said compound. It is to be understood that treatment includes prophylactic treatment of patients at risk in view of the protective properties observed.

Heteropolyanions such as heteropolytungstates are generally known, and reference is made to "Comprehensive Coordination Chemistry" Eds G Wilkinson et al, Pergamon 1987, vol 3 chapter 38. These compounds appear to be of essentially academic interest and not to have achieved any use in commerce. GBP 1,385,489 in the name of ANVAR states that certain of these compounds are useful in the formation of therapeutic preparations for the inhibition of the development of viruses which propagate by budding on the surface of infected cells. Typical of such viruses are stated to be leukemogenic and sarcomagenic viruses, rubella virus, vesicular stomatis virus and Myxoviruses and Paramyxoviruses including Rhinovirus. It is not believed that those compounds have been commercialised for the treatment of virus infections, nor is it believed that there has been any suggestion that any of the compounds could have activity against HIV. Certain of the compounds of the classes disclosed in said GBP do not appear to demonstrate selectivity against HIV-infected cells.

It has been suggested, in JP 64-38,022, that certain salts of heteropolyacid ions of general formula $(XM_{12}O_{40})^{P-}$ where X is an ion selected from Groups III to VI or transition metal, M is one to three species selected from Mo, W, Al, V, Nb, Ta, Co and Ti and P is a positive integer, exemplified by the two compounds $K_5BW_{12}O_{40}$ and $K_7PW_{10}Ti_2O_{40}$ which have activity against herpes virus, could be expected to have activity against human retrovirus. We are not aware that any of these compounds have been studied for activity against HIV, nor that any of the compounds are being developed for such use.

It has also been reported in Chemical and Engineering News, December 1986, that silicotungstate acid, $H_4SiW_{12}O_{40}$ has activity against HIV; this compound has, however, been abandoned because of its toxicity in higher animals.

We have now discovered certain polyoxometallate compounds which exhibit not only activity against HIV in the screening tests used, but also a relatively low toxicity against cells. Accordingly, the present invention provides as active compound for the various aspects of the invention, a compound selected from those containing ions of the Keggin structure, and defined by the general formula I or Ia $$A_x[MDLW_{11}O_{39}]\cdot yH_2O \qquad (I)$$

$$A_x[D'(MW_{11}O_{39})_2]\cdot yH_2O \qquad (Ia)$$

wherein
A is a cation,
x is an integer which varies with the element M and the oxidation state of element D or D',
M is boron, silicon or phosphorus,
D is a metal and D' is a lanthanide in oxidation state 3 or 4,
L is a neutral or anionic ligand, and
y is an integer,
provided that when D is a aluminium, vanadium or cobalt ion, L is not water.

Compounds of the class:

$$A_a[D'(M'W_{11}O_{39})_2]\cdot yH_2O$$

where
A, D' and y are as defined above,
M' is a phosphorus or silicon atom, and
a is an integer which depends on the oxidation state of D' and on element M',
have been reported, together with methods for their preparation in J. Chem. Soc.(A), (1971), 1836–1839. The compound $Na_{14}[Th(BW_{11}O_{39})_2]\cdot 38H_2O$ has been reported in Inorganic Syntheses, (1985), 23, 186–191, but we believe that the compounds of formula Ib:

$$A_a[D'(BW_{11}O_{39})_2]\cdot yH_2O \qquad (Ib)$$

in which a, D' and y are as defined above, are novel and hence form part of the present invention. These compounds may be prepared in manner analogous to that described in the art, by reacting a lacunary Keggin species of the formula $[BW_{11}O_{39}]^{9-}$ with a lanthanide salt in aqueous solution to form the desired compound Ib. Preferably, the $[BW_{11}O_{39}]^{9-}$ species is prepared in situ by reacting $Na_2WO_4\cdot 2H_2O$ with boric acid as described more particularly hereafter. Preferably, the reaction with the lanthanide salt is carried out at elevated temperature. The invention therefore also provides a process for the production of compounds Ib.

Suitable cations which may be present in the compounds of formula I, Ia and Ib include hydrogen, alkali metals such as potassium or sodium, alkaline earth metals, ammonium and substituted ammonium for example substituted by one, two, three or four alkyl or aryl groups, and other basic nitrogen-containing organic compounds such as amino acids or cyclic nitrogen-containing compounds. It is not believed that the cation is especially critical to activity, although it may have influence on toxicity. Examples of metal ions D include V,Ni,Co,Cu,Sn,Ga,Pt,Al,Rh and Zn and lanthanide atoms; D' may be selected from $Ce^{III}$, $Ce^{IV}$, Er, Pr and Gd for example. Suitable ligands include $H_2O$, methyl, ammonia and amines, including cyclic amines.

It will be appreciated that the above-identified compounds are capable of existing in aqueous solution in a number of equilibrium states according to the prevailing conditions, and although the compounds may be readily isolated only in certain salt forms, the active species in a biological environment may not easily be determined or indeed may be made available from a number of apparently different materials. All such variations are included within the scope of the present invention.

In particular, the value of y, representing the number of water molecules associated with the Keggin structure, is not critical, and may vary according to the degree of hydration of the compound.

Preferably, the compounds selected has a selectivity index as hereinafter defined in excess of 10, more preferably in excess of 50, for at least one of the HIV types.

The invention is illustrated by the preparation of compounds of formula Ib, and the testing of compounds of formula I or Ia, as will be more particularly described hereinafter.

PREPARATION OF $K_{15}[Er(BW_{11}O_{39})_2] \cdot yH_2O$ 36.3 g (0.11 mol) of $Na_2WO_4 \cdot 2H_2O$ was dissolved in 150 ml of water, and the pH adjusted to 6.5 with glacial acetic acid. Boric acid (3.6 g, 0.06 mol) was added and the solution was heated to 80° C. to form the $[BW_{11}O_{39}]^{9-}$ species in solution. The mixture was stirred for 10 mins before 2.22 g (5 mmol) of Er(-NO$_3$)$_3 \cdot 5H_2O$ in 20 ml of water was added, and heating continued for 15 mins. 20 g of KCl was added and the solution was allowed to cool to room temperature. A pink oil separated and the mixture was cooled in a refrigerator until crystallisation. The solid was collected by filtration and recrystallised from 50 ml of water at 70° C. The pink crystalline material was collected by filtration, washed with a little cold water, ethanol and diethylether and dried in vacuo. The yield of product was 18.5 g.

The same procedure was used to prepare the analogues containing $Ce^{III}$, Pr and Gd. The $Ce^{IV}$ analogue was prepared by oxidising the $Ce^{III}$ compound with $K_2S_2O_8$ in aqueous solution.

The compounds were tested in a screen by the MTT method (J. Virol. Methods 120: 309–321 [1988]). MT-4 cells ($2.5 \times 10^4$/well) were infected with HIV-1 (HTLV-IIIB) or HIV-2 (LAV-2 ROD) at a concentration of 100 $CCID_{50}$ and incubated in the presence of various concentrations of the test compounds, which were added immediately after infection with the virus. After 5 days culture at 37° C. in a $CO_2$ incubator, the number of viable cells was assessed by the MTT (tetrazolium) method. Antiviral activity and cytotoxicity of the compounds are expressed in the table below as $ED_{50}$ (ug/ml) and $CD_{50}$ (ug/ml), respectively. The potential therapeutic usefulness was assessed by calculating a Selectivity Index (SI) corresponding to the ratio of $CD_{50}$ to $ED_{50}$. A control test was performed using the compound HPA-23 ($NaSb_9W_{21}O_{86}$), known to be a reverse transcriptase inhibitor, and which has been used in clinical trials, and the known anti-HIV treatment AZT, and a number of comparison compounds were also run through the screen as detailed below.

TABLE

| | HIV-1 | | | HIV-2 | | |
|---|---|---|---|---|---|---|
| Compound | $CD_{50}$ | $ED_{50}$ | SI | $CD_{50}$ | $ED_{50}$ | SI |
| Comparisons | | | | | | |
| HPA-23 | 7.4 | 2.8 | 3 | 2.4 | >4 | <1 |
| AZT (μM) | >1 | <0.008 | >125 | ND | ND | ND |
| According to the Invention | | | | | | |
| $K_{13}[Ce(SiW_{11}O_{39})_2]26H_2O$ | >1000.0 | 0.39 | >2561 | >1000.0 | 0.157 | >6357 |
| $K_5[BPt(OH_2)W_{11}O_{39}]yH_2O$ | 327.9 | 1.66 | 198 | 301.3 | 6.21 | 49 |
| $K_6[SiNi(OH_2)W_{11}O_{39}]15H_2O$ | 198.43 | 1.93 | 103 | 198.43 | 3.58 | 55 |
| $K_6[BRh(OH_2)W_{11}O_{39}]14H_2O$ | 567.3 | 5.88 | 97 | 575.9 | 31.58 | 18 |
| $K_6[SiCu(OH_2)W_{11}O_{39}]yH_2O$ | 168.68 | <2.0 | >84 | >250.0 | <2.0 | >125 |
| $K_5[PCu(OH_2)W_{11}O_{39}]yH_2O$ | >250.0 | 3.04 | >82 | 136.1 | <2.0 | >68 |
| $K_6[SiCo(OH_2)W_{11}O_{39}]yH_2O$ | 104.94 | <2.0 | >52 | 30.52 | <2.0 | >15 |
| $K_7[BCo(OH_2)W_{11}O_{39}]yH_2O$ | 129.0 | 2.74 | 47 | 114.7 | >200.0 | <1 |
| $K_7[BCu(OH_2)W_{11}O_{39}]yH_2O$ | 113.3 | 3.51 | 32 | 157.8 | 2.56 | 62 |
| $K_5[PNi(OH_2)W_{11}O_{39}]14H_2O$ | 115.64 | >250.0 | <1 | 53.32 | >250.0 | <1 |
| $K_5[SiGa(OH_2)W_{11}O_{39}]yH_2O$ | 106.3 | 1.06 | 100 | 86.8 | 6.19 | 14 |
| $K_6[BGa(OH_2)W_{11}O_{39}]yH_2O$ | 618.1 | 0.12 | 5151 | 482.5 | 1.62 | 298 |
| A | >1000.0 | 1.99 | >502 | >1000.0 | 2.41 | >415 |
| B | 97.3 | 0.98 | 99 | 79.8 | 3.01 | 26 |
| C | 22.7 | 0.57 | 40 | 64.8 | 3.48 | 19 |

Notes:
ND = Not Determined
Compound A = $(C_5H_5NH^+)_6[SiCo(C_5H_5N)W_{11}O_{39}]yH_2O$
Compound B = $(C_6H_{11}NH_3^+)_6[SiCo(C_6H_{11}NH_2)W_{11}O_{39}]yH_2O)$
Compound C = $((CH_3)_3NH^+)_5[SiSn(CH_3)W_{11}O_{39}]yH_2O$ It will be seen from the above results that the compounds of general formula I exhibit selective activity against HIV in infected cells, and their toxicity is much less than HPA-23. Although AZT has a selectivity index of 125, this is at a rather high toxicity.

Compounds of particular interest for use in the various aspects of the present invention may be represented by formula Ic, $$A_x[Z] \cdot yH_2O \qquad (Ic)$$

in which A, x and y are as defined hereinbefore, and Z is selected from $Ce(SiW_{11}O_{39})_2$, $BPt(OH_2)W_{11}O_{39}$, $SiNi(OH_2)W_{11}O_{39}$, $BRh(OH_2)W_{11}O_{39}$, $SiCu(OH_2)W_{11}O_{39}$, $PCu(OH_2)W_{11}O_{39}$, $SiCo(OH_2)W_{11}O_{39}$, $BCo(OH_2)W_{11}O_{39}$, $BCu(OH_2)W_{11}O_{39}$, $SiGa(OH_2)W_{11}O_{39}$, $BGa(OH_2)W_{11}O_{39}$, $SiCo(C_5H_5N)W_{11}O_{39}$, $SiCo(C_6H_{11}NH_2)W_{11}O_{39}$ and $SiSn(CH_3)W_{11}O_{39}$.

The active compounds as defined may be administered in the form of pharmaceutical compositions formulated according to well known principles and incorporating the compound, preferably in unit dose form, in combination with a pharmaceutically acceptable diluent or excipient. Such compositions may be in the form of solutions or suspensions for injection or for irrigation, or be in capsule, tablet, dragee, or other solid composition or as a solution or suspension for oral administration or formulated into pessaries or suppositories or sustained release forms of any of the above or for implantation. Suitable diluents, carriers, excipients and other components are known. It may be desirable also to formulate a composition for topical administration such as an ointment or cream. The compounds of the invention may be used, in the form of a composition or alone, and possibly supported on a finely divided carrier, as a coating on devices or articles which in use contact body fluids, to discourage transmission of viral infections. Examples of devices and articles to be considered in this aspect of the invention are surgical devices and gloves and contraceptives such as condoms, and other items, appliances, wound dressings and coverings, implements etc.

The pharmaceutical compositions according to the invention may contain unit dosages determined in accordance with conventional pharmacological methods, suitably to provide active compound in the dosage range in humans of from 0.1 to 100 mg/kg body weight per day, in a single dose or in a number of smaller doses. Preferred dosage ranges are 1 to 30 mg/kg body weight per day. Other active compounds may be used in the compositions or administered separately or supplemental therapy may be included in a course of treatment for a patient.

We claim:

1. A method of treatment of patients infected by HIV, comprising administering to said patient an effective amount of a compound of formula, $$A_x[D'(MW_{11}O_{39})_2] \cdot yH_2O \qquad (Ia)$$

in which
A is a cation,
x is an integer which varies with the element M and the oxidation state of element D or D',
M is boron, silicon or phosphorus,
D is a metal and D' is a lanthanide in oxidation state 3 or 4,
L is a neutral or anionic ligand, and
y is an integer,
provided that when D is cobalt, vanadium or aluminium, L is not water.

2. The method as claimed in claim 1, wherein the compound of formula Ia is $K_{13}[Ce(SiW_{11}O_{39})_2]26H_2O$.

* * * * *